United States Patent
Parker

(10) Patent No.: US 6,762,322 B1
(45) Date of Patent: Jul. 13, 2004

(54) PREPARATION OF NITRONE DERIVATIVES

(75) Inventor: Dane Kenton Parker, Massillon, OH (US)

(73) Assignee: Goodyear Tire & Rubber Company, Akron, OH (US)

(*) Notice: Subject to any disclaimer, the term of this patent is extended or adjusted under 35 U.S.C. 154(b) by 0 days.

(21) Appl. No.: 10/324,199

(22) Filed: Dec. 20, 2002

(51) Int. Cl.$^7$ ............... C07C 249/00; C07C 249/02; C07C 249/04; C07C 249/12
(52) U.S. Cl. .................................. 564/253
(58) Field of Search ........................ 564/253

(56) References Cited

U.S. PATENT DOCUMENTS

| | | |
|---|---|---|
| 4,224,430 A | 9/1980 | Maekawa |
| 5,622,994 A | 4/1997 | Carney |
| 5,723,502 A | 3/1998 | Proctor |
| 6,002,001 A | 12/1999 | Carney |
| 6,107,315 A | 8/2000 | Carney et al. |
| 6,255,448 B1 | 7/2001 | Grimaldi et al. |
| 6,291,702 B1 | 9/2001 | Becker |
| 6,333,381 B1 | 12/2001 | Asada |

FOREIGN PATENT DOCUMENTS

| | | |
|---|---|---|
| WO | WO 99/20601 | 4/1999 |
| WO | WO 00/02848 | 1/2000 |

OTHER PUBLICATIONS

Bigdeli et al., Phosphorus, Sulfur and Silicon, 2002, 177(10), p. 2309–2314.*
Tiollais, Bull. Soc. Chim. Fr. 1947, p. 708–716.*
Pyne et al., J. Org. Chem. 1990, 55, p. 1932–1936.*
Hajipour et al, *A Rapid and Efficient Synthesis of Oxaziridines and Diaryl Nitrones Using Oxone*, J. Chem. Research(S), 1992, 388.
Janzen et al, *Detection and Identification of Short–Lived Free Radicals by Electron Spin Resonance Trapping Techniques (Spin Trapping) Photolysis of Organolead, –tin, and mercury Compounds*, JACS, 91, 4481 (1969).
Cox, *Detection and Identification of Short–Lived Free Radicals by an Electron Spin Resonance Trapping Technique*, JACS, 90, 5909 (1968).
Huie et al, *Facile One–Step Synthesis of Phenyl–ter–butylnitrone(PBN) and Its Derivatives*, J. Org. Chem. 1985, 50, 1531–1532.
Grishin et al, *Problems of Control of the Reactivity of Macroradicals and the Growth of Polymer Chains*, Russian Chemical Review 70 (5) 425–447 (2001).
NeoGen Research Corporation, <URL http://www.neogen-research.com/product–orders.shtml< pp 1–6, Nov. 10, 2002.
Kolyakina et al, *Effect of C–Pheyl–N–tert–butylnitrone Additives on the Radical Polymerization of Butyl Acrylate and Butyl Methacrylate*, Polymer Science, Ser. A. vol. 43, No. 12, 2001, pp. 1223–1227.
Grishin et al, *Nitrones as New Regulating Agents for Polymer Chain Propagation*, Polymer Science, Ser. A. vol. 41, No. 4, 1999, pp 401–405.
Risnik et al, *Nitrons as Modifiers and Molecular Weight Regulators in Radical Polymerisation*, Kauchuk i Rezlna, No. 6, 1999, p. 41.
Grishin et al, *Experimental and Theorectical Quantum-Chemical Study of Radical Polymerization in the Presence of Nitroxyl Radicals*, Polymer Science, Ser. A vol. 43, No. 10, 2001, pp. 989–994.
Murahashi et al, *Tungstate–Catalyzed Oxidation of Secondary Amines to Nitrones, Alpha–Substitution of Secondary Amines via Nitrones*, J. Org. Chem., 1990, pp 1735–1744.
Christensen et al, *Oxidation of Imines to Nitrones by the Permangante Ion*, J. Org. Chem. 1989, 54, 125–131.

* cited by examiner

Primary Examiner—Brian Davis
(74) Attorney, Agent, or Firm—Wood, Herron & Evans LLP

(57) ABSTRACT

Nitrone derivatives are efficiently prepared by increasing reagent concentrations in reaction solutions. Aldehydes and amines may be condensed to prepare an imine intermediate. Elimination of the solution media generally renders the imine formation more efficient. The imine is then reacted with a peroxysulfacte oxidizing agent in a solution having at least about 0.1M concentration of the imine. The oxaziridine is rearranged to produce the nitrone derivative in high yield and good purity.

20 Claims, No Drawings

PREPARATION OF NITRONE DERIVATIVES

BACKGROUND OF THE INVENTION

1. Field of the Invention

The present invention is directed toward a method of preparing nitrone derivatives, and in particular, for preparing nitrone derivatives from a imine intermediate.

2. Description of the Related Art

Nitrones are useful intermediates in a wide variety of applications. For example, nitrones are important as intermediates in organic synthesis, particularly in [3+2] cyclo addition reactions. Nitrones are excellent 1,3-dipoles and capable of reacting with double and triple bonds to form 5-membered heterocyclic ring structures. For example, isoxazolines and isoxazoles are formed by reacting nitrones with carbon-carbon double and triple bonds respectively. Accordingly, nitrones have been utilized for synthesizing various nitrogen containing biologically active compounds, for example, antibiotics, alkyloids, amino sugars, and beta-lactams.

In addition, nitrones are also known for their ability to act as efficient free radical "spin traps". Nitrones behave as spin trapping agents when a diamagnetic nitrone (the spin trap) reacts with a transient free radical (having a spin) to provide a more stable free radical (referred to as the spin adduct). More specifically, a very reactive oxygen-centered or carbon-centered free radical reacts with the nitrone to generate a new and very stable nitroxide radical adduct. The radical adduct generated may be detectable by electron para-magnetic resonance (EPR) spectroscopy if the stabilized free radical has a reasonable lifetime. Further, information about a spin of a radical can be gleaned from a study of the structure and spectroscopic characteristics of the new radical adduct due to the increased radical stability and lifetime. Thus, techniques utilizing nitrone spin trapping agents are an important method for garnering information on free radicals otherwise difficult or impossible to detect by direct spectroscopic observation due to their exceedingly short lifetimes and low concentrations.

Techniques utilizing nitrone spin trapping agents are also useful for studying free radical responses in biological systems. For example, the toxicity of a synthetic beta amyloid peptide preparation towards glutamine synthesis could be correlated with the characteristics of an EPR signal generated by the spin adduct formed from each batch of synthetic beta amyloid peptide and spin trap. U.S. Pat. No. 6,107,315, issued to Carney, discloses the use of a spin trapping reagent, such as α-phenyl-N-tert-butyl nitrone (PBN), in a suitable pharmaceutical carrier for administration to a patient for the treatment of symptoms associated with aging or other conditions associated with oxidative tissue damage. U.S. Pat. No. 5,723,502, issued to Proctor, discloses a method for ameliorating a cellular dysfunction of a tissue, such as the cosmetic treatment of hair loss and stimulation of hair growth, by administering a nitrone spin trap, such as PBN, to the affected tissue.

More recently, the usefulness of free radical/nitrone reactions has been exploited outside the biological field in the areas of rubber antioxidant protection, controlled radical polymerizations, and polymer/filler interactions. Nitrone derivatives as spin trapping agents are useful in controlling or regulating the rate of polymerization in a polymerization reaction. More specifically, the presence of a stable nitrone free radical during the polymerization or copolymerization of monomers provides for control of polymerization and results in polymers having a relatively narrow polydispersity, relative to polymers formed in the absence of a stable nitrone free radical. For example, U.S. Pat. No. 6,333,381 issued to Asada discloses the use of PBN to control the polymerization of various types of rubbers.

There are many proposed methods for the synthesis of nitrone derivatives. One proposed method prepares nitrones directly by condensing an aldehyde and a hydroxylamine. Comprehensive Organic Chemistry, vol. 2, pp 196–201, Pergamon Press, (1979). This reference specifically teaches the condensation of benzaldehyde and N-t-butyl hydroxylamine to produce PBN and water. However, many hydroxylamines are either unstable, unavailable and/or expensive. N-t-butyl hydroxylamine, in particular, can be prepared by the reduction of 2-methyl 2-nitropropane, a relatively expensive starting material, with zinc-amalgam or aluminum-amalgam, both of which are heavy metal salt catalysts which present environmental hazards and other problems related to disposal. Another proposed method involves a one-pot generation of PBN from benzaldehyde and 2-methyl 2-nitropropane. Journal of Organic Chemistry, vol. 50, pg. 1531 (1985). This method, while simple to conduct on a small scale is costly to scale-up due to the use of expensive 2-methyl 2-nitropropane and zinc as a catalyst. The zinc presents the disposal drawbacks discussed above.

Exotic catalysts have been developed and utilized in an effort to efficiently prepare nitrone derivatives directly from starting materials. In one method, nitrones have been prepared by oxidizing alkyl-alpha-amino acids with a tungstate catalyst in dichloromethane. Journal of Organic Chemistry, vol. 59, pg. 6170 (1994). Similarly, methyl trioxorhenium (MTO) has been used as a catalyst to oxidize secondary amines directly to nitrones. Journal of Organic Chemistry, vol. 61, pg. 8099 (1996). Still further, permanganate oxidizing agents have been proposed for producing nitrones by directly oxidizing an amine to a nitrone. Journal of Organic Chemistry, vol. 54, pg. 126 (1989). However, these methods suffer from the use of expensive heavy-metal catalysts, chlorinated and toxic solvents, strongly acidic and dangerous oxidizing agents, and/or commercially unavailable starting materials, all of which adds to the time and effort involved in preparing the nitrone derivatives. Further, the use of heavy-metal catalysts limits the utility of these methods on a large scale because of the large amounts of catalyst required and costs involved.

In addition to the proposals for the direct preparation of nitrone derivatives from aldehyde starting-materials, multi-step procedures have been proposed. See, for example, European Patent No. WO 0002848. However, these processes suffer from drawbacks. Each reaction intermediate must generally be purified. Additionally, azeotropic solvents, such as toluene, are used to remove water in a lengthy and time-consuming reaction. Further, expensive oxidizing agents are used. For example, one method uses meta-chloroperbenzoic acid (m-CPBA) as an oxidizing agent, which is converted to its sodium salt during the oxidation reaction. This by-product must be separated and discarded prior to performing the next step.

Thus, there is a need to provide a method for the preparation of nitrone derivatives, such as PBN, which omits the use of heavy-metal catalysts and oxidizing agents that are hazardous and expensive. Further, it is desirable to provide a method which utilizes inexpensive starting materials. Still further, it is desirable to provide a method which is efficient and cost-effective on a commercial scale.

SUMMARY OF THE INVENTION

The present invention overcomes the above-mentioned drawbacks by providing an efficient method for the preparation of nitrone derivatives. To this end, and in accordance with the principles of the present invention, one aspect of the invention is directed to a method of preparing nitrone derivatives having a general formula (I)

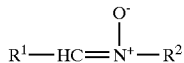

wherein $R^1$ and $R^2$, are independently selected from the group consisting of substituted or unsubstituted straight, branched, or cyclic alkyl, alkenyl, alkynyl, aryl, heteroaryl, alkaryl, alkoxyl, halo-alkyl, and combinations thereof. Alternatively, $R^1$ and $R^2$ taken together with the carbon and nitrogen to which they are attached form a 5–8 membered ring. The method includes the steps of:

reacting an imine compound having a general formula (II)

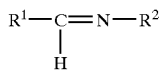

wherein $R^1$ and $R^2$ are as defined above, with an oxidizing agent having a general formula (III)

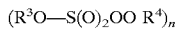

wherein $R^3$ and $R^4$, independently, are selected from the group consisting of $NH_4$, Na, K, Li, and a substituted or unsubstituted straight, branched or cyclic $C_1$–$C_{10}$, alkyl, and n is an integer selected from 1, 2, and 3, in an inert solution to form an oxaziridine compound having a general formula (IV)

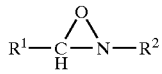

wherein $R^1$ and $R^2$ are as defined above and the imine compound of formula (II) is present in a concentration of at least about 0.1M in the solution; and rearranging the oxaziridine compound of formula (IV) to form a nitrone compound of formula (I).

Another aspect of the invention is directed to a method of preparing nitrone derivatives having a general formula (VII)

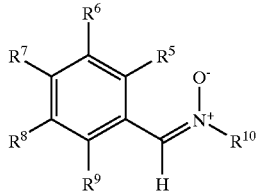

wherein $R^5$, $R^6$, $R^7$, $R^8$ and $R^9$ are independently selected from the group consisting of H, substituted or unsubstituted straight, branched, or cyclic alkyl, alkenyl, alkynyl, aryl, heteroaryl, alkaryl, alkoxyl, halo, cyano, nitro, and combinations thereof, alternatively any two adjacent $R^5$, $R^6$, $R^7$, $R^8$ and $R^9$ groups taken together with the carbons to which they are attached form a 5–8 membered ring including 0–2 heteroatoms selected from the group consisting of O, N, and S, and $R^{10}$ is a substituted or unsubstituted straight, branched, or cyclic alkyl, the method comprising the steps of:

(a) reacting an aldehyde compound having a general formula (VIII)

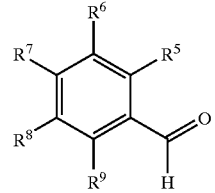

wherein $R^5$, $R^6$, $R^7$, $R^8$ and $R^9$ are as defined in general formula (VII), with an amine compound having a general formula (IX)

wherein $R^{10}$ is as defined in general formula (VII), to form an imine compound having a general formula (X)

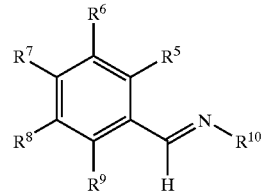

wherein $R^5$, $R^6$, $R^7$, $R^8$, $R^9$ and $R^{10}$ are as defined in general formula (VII);

(b) reacting the imine compound of formula (X) with an oxidizing agent having a general formula (XI)

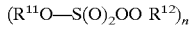

wherein $R^{11}$ and $R^{12}$, independently, are selected from the group consisting of $NH_4$, Na, K, Li, and straight, branched or cyclic $C_1$–$C_{10}$ alkyl, and n is an integer selected from 1, 2, and 3, in an inert solution having at least about 0.1M concentration of the imine compound in the solution, to form an oxaziridine compound having a general formula (XII)

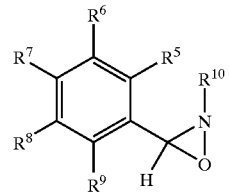

wherein $R^5$, $R^6$, $R^7$, $R^8$, $R^9$ and $R^{10}$ are as defined in general formula (VII); and (c) rearranging the oxaziridine compound of formula (XII) to form the nitrone compound of formula (VII).

Surprisingly and unexpectedly, an imine may be efficiently and effectively converted to a corresponding oxaziridine at high concentrations in solution. Particularly, imine concentrations of at least about 0.1M (molar concentration) or higher in the reaction solution enhance the rate of the oxaziridine formation. Advantageously, the imine concentration may be in a range of from about 0.1M to about 1.0M, and more advantageously from about 0.5M to about 1.0M. High imine concentrations provide a savings in terms of reagent costs and time. These savings generally magnify as the scale of the nitrone preparation increases.

The imine is oxidized with a peroxysulfate oxidizing agent to form an oxaziridine. Advantageously, the oxidizing agent is a mono-peroxy sulfate compound. In one embodiment of the present invention, the oxidizing agent is a potassium monoperoxysulfate compound commercially available from the Aldrich Chemical Co., Milwaukee, Wis., and sold under the brand name of Oxone®. Oxone® is inexpensive relative to the prior art catalysts and forms the oxaziridine quickly depending on the concentration of the reagents in solution. Oxone® readily lends itself to large-scale preparations.

The oxaziridine intermediate is then rearranged to open the oxaziridine ring and form the desired nitrone derivative. Rearrangement may be accomplished in a variety of conventional methods, such as for example, by the use of heat in the presence of a high-boiling solvent, such as toluene or xylene. In one embodiment of the present invention, thermal rearrangement occurs in a temperature range of from about 110° C. to about 150° C. In another embodiment, thermal rearrangement occurs absent a diluent or solvent-medium, thereby providing a crude, reasonably pure nitrone derivative in high yield. The rearrangement generally occurs rather quickly and may be complete in as little as 15 minutes or it may require a few hours. Omission of a solvent generally reduces reaction time.

The imine starting material may be commercially purchased or synthetically prepared. If desired, the imine may be prepared by a condensation reaction between an aldehyde and a primary amine. In one embodiment of the present invention, the imine precursor for α-phenyl-N-tert-butyl nitrone (PBN) is prepared by combining benzaldehyde and t-butyl amine at room temperature, in the absence of a solvent, to form the corresponding benzylidene-t-butyl amine (imine) and water. It was found that the resulting imine was sufficiently pure for use in the next step without the need for purification or removal of water by-product contained therein. Thus, the present method reduces time and cost, and improves efficiency, in comparison with traditional transformations.

By virtue of the foregoing, there is provided an efficient method for the preparation of nitrone derivatives that does not suffer from the drawbacks and weaknesses of traditional methods. In addition, the imine and oxaziridine formation may be performed in a single reaction vessel. By utilizing high concentrations of materials in each reaction, and in particular, by increasing the concentration of the imine in the solution, the present method provides advantages over traditional methods. Particularly, the nitrone derivatives may be prepared in high yields without costly side-products warranting removal. In many cases, the imine and oxaziridine intermediates and nitrone derivative need not be purified. By eliminating the need for a solvent medium, the rearrangement reaction may be carried out in a cost-effective and time-effective manner. Still further, the present method may be scaled up to prepare large, industrial volumes. These and other benefits and advantages of the present invention shall be made apparent by the accompanying description of the preferred embodiments of the invention.

DETAILED DESCRIPTION OF THE PREFERRED EMBODIMENTS OF THE INVENTION

The present invention provides an efficient method of preparing nitrone derivatives. In accordance with one aspect of the invention, nitrone derivatives having a general formula (I)

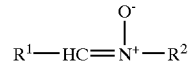

wherein $R^1$ and $R^2$, independently, may be substituted or unsubstituted straight, branched, or cyclic alkyl, alkenyl, alkynyl, aryl, heteroaryl, alkaryl, alkoxyl, halo-alkyl, or combinations thereof, or alternatively, $R^1$ and $R^2$ taken together with the carbon and nitrogen to which they are attached form a 5–8 membered ring, may be prepared by the present method including the steps of:

reacting an imine compound having a general formula (II)

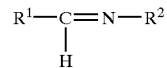

wherein $R^1$ and $R^2$ are as defined above, with an oxidizing agent having a general formula (III)

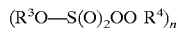

wherein $R^3$ and $R^4$, independently, are selected from the group consisting of $NH_4$, Na, K, Li, and a substituted or unsubstituted straight, branched, or cyclic $C_1$–$C_{10}$ alkyl, and n is an integer selected from 1, 2, and 3, in a solution to form an oxaziridine compound having a general formula (IV)

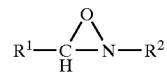

wherein $R^1$ and $R^2$ are as defined above, and the imine compound is in a concentration of at least about 0.1M in the solution; and rearranging the oxaziridine compound of formula (IV) to form the nitrone compound in formula (I).

In accordance with another aspect of the invention, nitrone derivatives having a general formula (VII)

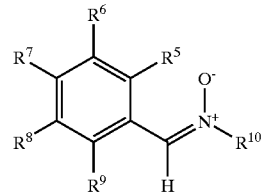

wherein $R^5$, $R^6$, $R^7$, $R^8$ and $R^9$ are independently selected from the group consisting of H, substituted or unsubstituted straight, branched, or cyclic alkyl, alkenyl, alkynyl, aryl, heteroaryl, alkaryl, alkoxyl, halo, cyano, nitro, and combinations thereof, alternatively any two adjacent $R^5$, $R^6$, $R^7$, $R^8$ and $R^9$ groups taken together with the carbons to which they are attached form a 5–8 membered ring including 0–2 heteroatoms selected from the group consisting of O, N, and S, and $R^{10}$ is a substituted or unsubstituted straight, branched, or cyclic alkyl, may be prepared by a method including the steps of:

(a) reacting an aldehyde compound having a general formula (VIII)

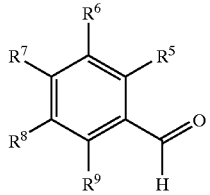

wherein $R^5$, $R^6$, $R^7$, $R^8$ and $R^9$ are as defined in general formula (VII), with an amine compound having a general formula (IX)

wherein $R^{10}$ is as defined in general formula (VII), to form an imine compound having a general formula (X)

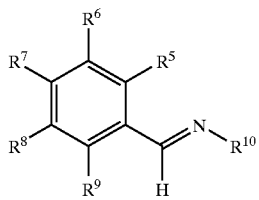

wherein $R^5$, R6, $R^7$, $R^8$, $R^9$ and $R^{10}$ are as defined in general formula (VII);

(b) reacting the imine compound of formula (X) with an oxidizing agent having a general formula (XI)

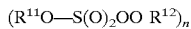

wherein $R^{11}$ and $R^{12}$, independently, are selected from the group consisting of $NH_4$, Na, K, Li, and straight, branched or cyclic $C_1$–$C_{10}$ alkyl, and n is an integer selected from 1, 2, and 3, in a solution having at least about 0.1M concentration of the imine compound in the solution, to form an oxaziridine compound having a general formula (XII)

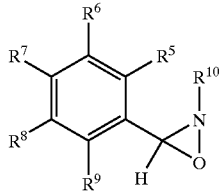

wherein $R^5$, $R^6$, $R^7$, $R^8$, $R^9$ and $R^{10}$ are as defined in general formula (VII); and (c) rearranging the oxaziridine compound of formula (XII) to form the nitrone compound of formula (VII).

The present method is inexpensive relative to traditional methods by eliminating the use of costly and hazardous metal catalysts, such as tungsten, rhenium, and manganese. The present method is also more efficient than traditional methods by reducing or eliminating time and labor related to separating and purifying individual intermediates after each step in the method. The present method is useful for the preparation of α-aryl-N-alkyl nitrone derivatives, such as phenyl tert-butyl nitrone (PBN). PBN has a multitude of uses as previously disclosed herein. Moreover, PBN is the only nitrone listed on the U.S. government's TSCA list, a list which includes compounds that have been federally approved in terms of safety and industrial scale preparations for further use.

The term "derivative", as used herein, is intended to refer to a compound resulting when one or more desirable substitutions are attached to a core functional group. To this end, the term "nitrone derivative", as used herein, is intended to refer to compounds having a nitrone functional core, as illustrated in the general formula (I) and (VII) above. Accordingly, the term "nitrone derivatives" encompass all compounds formed where the R group substitutions of the general formulae (I) and (II) are independently selected from substituted or unsubstituted straight, branched, or cyclic alkyl, alkenyl, alkynyl, aryl, heteroaryl, alkaryl, alkoxyl, haloalkyl, and combinations thereof, while the R group substitutions of formulae (VII) and (X) above may further include cyano and nitro substitutions. The term "alkyl", as used herein, is intended to refer to monovalent, saturated groups that are straight, branched or cyclic in structure and may comprise only carbon atoms, such as from 1 to about 10 carbon atoms, or may also include heteroatoms, such as for example, nitrogen (N), oxygen (O), and sulfur (S). For example, the alkyl substitution of α-phenyl-N-tert-butyl nitrone (PBN) is a tert-butyl group (a branched alkyl) attached to the nitrogen atom of the nitrone functional core. Examples of other alkyl groups include methyl, ethyl, n-propyl, isopropyl, n-butyl, isobutyl, n-hexyl, n-octyl, tert-octyl and the like. The alkyl substitution may further include generally non-reactive functional groups, such as a ketone, an ether, an ester, and an amide. The term "alkenyl", as used herein, is intended to refer to unsaturated organic substitutions having one or more double bonds in the structure. Examples of alkenyl groups include, without limitation, ethenyl (—CH=$CH_2$), n-propenyl (—$CH_2$CH=$CH_2$), and isopropenyl (—C($CH_3$)=$CH_2$). The term "alkynyl", as used herein, is intended to refer to unsaturated organic substitution having one or more triple bonds in the structure. Examples of alkynyl groups include, without limitation, ethynyl, propargyl, and the like. The term "aryl", as used herein, is intended to refer to an unsaturated aromatic carbocyclic group from 6 to 14 carbon atoms having a single ring (e.g. phenyl) or multiple rings (e.g., naphthyl and anthryl). Unless otherwise constrained by the definition for the individual substituent, such aryl groups can be optionally be substituted with from 1 to 3 substituents selected from the group consisting of alkyl, alkoxy, alkaryloxy, alkenyl, alkynyl, amino, aminoacyl, amincarbonyl, alkoxycarbonyl, aryl, carboxyl, cycloalkoxy, cyano, halo, hydroxy, nitro, trihalomethyl, thioalkoxy, and the like. The term "heteroaryl", as used herein, is intended to refer to an aryl group containing one or more heteroatoms selected from O, N, and S. Examples of heteroaryl groups include thiazoles, oxazoles and pyridines. The term "heteroaryl" further includes multiple rings, such as fused ring structures (e.g., quinoline). The term "alkaryl", as used herein, is intended to refer to -alkylene-aryl groups having 1 to 20 carbon atoms in the alkylene moiety and from 6 to 14 carbon atoms in the aryl moiety. Examples of alkaryl groups include, without limitation, benzyl, phenethyl, and the like. The term "alkoxyl", as used herein, is intended to refer to the group "alkyl-O—". An ether group would constitute an alkoxyl substitution. Examples of alkoxy groups include, without limitation, methoxy, ethoxy, n-propoxy, isopropoxy, n-butoxy, tert-butoxy, sec-butoxy, n-pentyloxy, n-hexyloxy and the like. The term "alkaryloxy" refers to —O-alkylene-aryl groups, such as benzyloxy, phenethyloxy, and the like. The term "cyano", as used herein, is intended to refer to the group —CN. The term "halo" or "halogen", as used herein, is intended to refer to fluoro, chloro, bromo and iodo groups. The term "nitro" refers to the group —NO$_2$. It is also contemplated that one or more halogens may be substituents on the alkenyl, aklynyl, aryl and heteroaryl groups as well. Accordingly, examples of nitrone derivatives include linear nitrone compounds such as N-alkyl-α-alkyl nitrones (e.g., N-methyl-α-methyl nitrone or N-methyl-α-ethyl nitrone), N-alkyl-α-aryl nitrones (e.g., N-methyl-α-phenylnitrone, N-ethyl-α-phenylnitrone, N-isopropyl-α-phenylnitrone, N-isobutyl-α-phenylnitrone, N-s-butyl-α-phenylnitrone, N-t-butyl-α-phenylnitrone (PBN), N-t-pentyl-α-phenylnitrone), N-alkyl-α-cycloalkylnitrones (e.g., compounds corresponding to the N-alkyl-α-arylnitrone listed above such as N-isopropyl-α-cyclohexylnitrone, N-t-butyl-α-cyclohexynitrone, N-t-penyl-α-cyclohexylnitrone), and N-aryl-α-arylnitrone (e.g., N-phenyl-α-phenylnitrone).

Alternatively, $R^1$ and $R^2$ of formula (I) may be joined together to form a ring structure containing the nitrone core therein. For example, the $R^1$ and $R^2$ substitutions may be joined together to form a 5-membered pyrroline-nitrone or a 6-membered piperidinyl-nitrone derivative. The ring structure including the carbon and nitrogen atoms to which the $R^1$ and $R^2$ are attached, respectively, may be as small as a 5-membered ring or as large as an 8-membered ring. Further, it is contemplated herein that where $R^1$ and $R^2$ are joined to form a ring structure, the ring may be one of aromatic, non-aromatic and condensed rings (e.g., quiniline, isoquinoline, indoline, and naphthyl-type nitrone derivatives) and further, the same or different carbon atoms each constituting the ring may be substituted with one or a plurality of substituents such as an alkyl group(s). Accordingly, examples of cyclic nitrone compounds include pyrroline N-oxides (e.g., 1-pyrroline-N-oxide, 5,5-dimethyl-1-pyrroline-N-oxide (DMPO), 5,5-diethyl-1-pyrroline-N-oxide, 4,4diethyl-1-pyrroline-N-oxide, 3,3-dimethyl-1-pyrroline-N-oxide), pyrrole-N-oxide, and piperazine-N-oxide.

Alternatively, any two adjacent $R^5$, $R^6$, $R^7$, $R^8$ and $R^9$ groups of formula (VII) taken together with the carbons to which they are attached may be joined together form ring including 0–2 heteroatoms selected from the group consisting of O, N, and S. The ring structure including the carbon atoms to which the two R substitutions are attached may be as small as a 5-membered ring or as large as an 8-membered ring, fused to the phenyl. Further, it is contemplated herein that where two R groups are joined to form a ring structure, the ring may be one of aromatic, non-aromatic and condensed rings. For example, adjacent R substitutions may be joined together to form an indole or a quinoline heteroaryl as the "aryl" group of the nitrone. Further examples include, without limitation, isoquinoline, indoline, and naphthyl fused ring systems. In addition, any of the atoms constituting the ring may be substituted with one or more substituents, such as an alkyl group(s). It should be understood by persons of ordinary skill in the art that the $R^1$, $R^2$, $R^5$, $R^6$, $R^7$, $R^8$, $R^9$ and $R^{10}$ substitutions will not contain groups that are more reactive to the oxidizing agent than the imine targeted for conversion to the oxaziridine ring.

The oxidizing agent is a peroxysulfate compound having a general formula (III) $(R^3O—S(O)_2OO\ R^4)_n$ or general formula (X) $(R^{11}O—S(O)_2OO\ R^{12})_n$ wherein $R^3$, $R^4$, $R^{11}$ and $R^{12}$, independently, are selected from the group consisting of $NH_4$, Na, K, Li, and substituted or unsubstituted straight, branched, or cyclic $C_1$–$C_{10}$ alkyl, wherein n is an integer selected from 1, 2, and 3. The peroxysulfate group oxidizes the unsaturated imine group to the corresponding oxaziridine ring. Advantageously, the peroxysulfate compound is a monoperoxysulfate compound wherein n is 1. More advantageously, the peroxysulfate compound is a potassium monoperoxysulfate compound, such as Oxone®, commercially available from Aldrich Chemical Co., Milwaukee, Wis. Oxone® is a mixture of potassium monoperoxysulfate and two other sulfate groups associated therewith to stabilize the sulfate-peroxide. To this end, other suitable peroxysulfate compounds may be stabilized with one or more stabilizing groups. It should be understood that such stabilizing groups in the peroxysulfate compound should not be reactive with the imine or detrimental to the formation of the oxaziridine ring. Peroxysulfates in general, and Oxone® in particular, are less expensive than the metal catalysts of the prior art. In addition, they do not present environmental problems associated with disposal, and sulfate by-products are water soluble and easily separated from the oxaziridine intermediate by simply washing the reaction mixture with water.

The oxaziridine is formed by reacting the imine with the oxidizing agent. Oxaziridine formation generally occurs in a solution media. However, in one aspect of the present invention, the solution contains the imine in a solution concentration of at least about 0.1M (molar concentration; moles of the imine per liter of the solution). Surprisingly and unexpectedly, it has been found that a high concentration of the imine in the solution allows the oxaziridine to form more quickly than prior art methods and at ambient conditions in the presence of the oxidizing agent. Moreover, higher concentrations allow for less solvent, less work-up and faster reaction times. To this end, the imine will advantageously be present in the solution in a concentration range of from about 0.1M to about 1.0M, and more advantageously, from about 0.5M to about 1.0M. Such high imine concentrations in solution render the present preparation of nitrone derivatives more efficient than prior art methods. Generally, reaction times are short and the oxaziridines are easily isolated. Further, high solution concentrations containing prior art metal catalysts and oxidizing agents often presented problems associated with the control and yields of the reactions. The benefits of the high imine concentrations of the present invention are particularly useful for large-scale preparations, especially where time is of the essence.

The solution or medium of reaction for forming the oxaziridine may vary, as may the precise reaction reagents and conditions. Advantageously, the solution comprises a 1:1 volume ratio of water and acetone with excess bicarbonate to render the solution slightly basic. By way of example, sodium or potassium bicarbonate may be used. The imine is dissolved into an amount of the solution sufficient to have a concentration of at least about 0.1M in the solution, and more advantageously to a concentration in the range of from about 0.5M to about 1.0M. A slight molar excess amount of peroxysulfate oxidizing agent, such as Oxone®, may then be added to the solution at or below room temperature over a period of time. Upon addition, the reaction is generally exothermic. Therefore, the oxidizing agent should be added in small portions at desired time intervals until the addition is complete. Portion-wise addition allows control of the reaction temperature preventing high-temperature decomposition of the imine and any oxaziridine in the solution. The formation of the oxaziridine at such highly concentrated solutions is almost instantaneous, requiring as little as 15 minutes to about an hour to go to completion. The present method is useful for the preparation of α-aryl-N-alkyl nitrones, such as PBN.

The oxaziridine intermediate formed above is then rearranged to form the corresponding nitrone derivative. This rearrangement may be brought about by a number of conditions and methods commonly used in the art. For example, the rearrangement may be effected by the addition of heat, so as to thermally rearrange the oxaziridine ring to the corresponding nitrone. In one embodiment of the present invention, the oxaziridine is subjected to heat in the range of from about 110° C. to about 150° C. for a short period of time, such as from 1 to 10 hours, to effect rearrangement. The rearrangement is also generally exothermic and, therefore, contributes to the total heat supplied to the reaction. It will be understood that different oxaziridine derivatives will require different time periods and different amounts of heat to rearrange. Particularly, it is noted that the more sterically hindered, strained, or generally unstable the oxaziridine ring intermediate is, the less heat and energy is required to rearrange the ring to the corresponding nitrone. Also, ground state kinetics of the resulting nitrone derivative will influence the kinetics of the rearrangement and determine the heat and times necessary for completion of the reaction, as well as formation of by-products.

Thermal rearrangement conditions including a solvent-medium are suitable. For example, thermal rearrangement may be accomplished in a suitable high-boiling solvent, such as toluene, with or without the aid of a boiling chip. In addition, the oxaziridine is advantageously present in a high concentration, such as from about 1.0M to about 5.0M in the solvent, so as to effectively rearrange and form the nitrone in a time-efficient manner. Alternatively, the rearrangement may be conducted without the use of a solvent medium. It has been found that rearranging the oxaziridine in the absence of a diluent, such as the toluene used above, enhances the rate of the rearrangement, relative to methods utilizing a diluting solvent. Furthermore, elimination of the solvent also eliminates the risk of the solvent participating in the reaction to contribute an undesirable by-product. Conversion of the oxaziridine to the corresponding nitrone in a highly concentrated solvent or without a diluent provides good yields of a crude nitrone product that is reasonably pure even without purification.

The imine starting material used for preparation of the nitrone may be commercially purchased or synthetically prepared. For example, one method of preparing imine derivatives involves the condensation of an aldehyde with a primary amine in the presence of a suitable solvent. In one embodiment of the invention, an imine of general formula (II) is prepared by condensing an aldehyde compound having a general formula (V)

wherein $R^1$ is as defined herein, with an amine compound having a general formula (VI)

wherein $R^2$ is as defined herein. Further, the imine may be formed from an aldehyde and an amine on a single organic structure. For example, $R^1$ may be attached to $R^2$ with a linker between the aldehyde and the amine such that a condensation reaction may occur between the aldehyde and the amine to form a cyclic imine. For example, a substituted or unsubstituted 1-amino-butyl carboxaldehyde may self-condense to form the corresponding 5-membered cyclic imine. Accordingly, the linker between $R^1$ and $R^2$ may be as small as a single atom (forming a cyclic imine of five atoms) or as large as 4 atoms (forming a cyclic imine of eight atoms) and may comprise only carbon atoms or include 0–1 heteroatoms selected from N, O, and S.

In another embodiment of the invention, an imine of general formula (X) is prepared by condensing an aldehyde compound having a general formula (VIII)

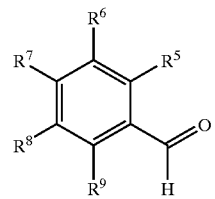

wherein $R^5$, $R^6$, $R^7$, $R^8$ and $R^9$ are independently selected from the group consisting of H, substituted or unsubstituted straight, branched, or cyclic alkyl, alkenyl, alkynyl, aryl, heteroaryl, alkaryl, alkoxyl, halo, cyano, nitro, and combinations thereof, and alternatively any two adjacent $R^5$, $R^6$, $R^7$, $R^8$ and $R^9$ groups taken together with the carbons to which they are attached form a 5–8 membered ring including 0–2 heteroatoms selected from the group consisting of O, N, and S, with an amine compound having a general formula (IX)

wherein $R^{10}$ is a substituted or unsubstituted straight, branched, or cyclic alkyl.

It has been found that certain aldehydes readily and spontaneously condense with amines, particularly primary amines, to form an imine. Spontaneous condensation can occur without the input of a form of energy, such as heat, solvent or a catalyst to bring about the imine formation. For example, in the formation of PBN, benzaldehyde spontaneously condenses with t-butylamine to form the corresponding imine. Traditional methods of forming the imine intermediate for PBN have involved condensation techniques involving the removal of the "water of formation" during the condensation, such as the use of a dean stark trap in conjunction with a high-boiling solvent, such as toluene, capable of azeotropically removing water. The present method, however, improves upon the traditional methods in terms of time and costs. For example, in one aspect of the present invention, benzaldehyde and t-butylamine are condensed in the absence of a solvent to efficiently and effectively form the imine without the need to remove the water formed during condensation. Removal of the water by-product has proven to kinetically drive condensation reactions to completion. However, the 'neat' condensations of the present methods can result in spontaneous imine formation at ambient conditions, such as room temperature, to produce imine derivatives in very high yields and in some cases, completely, despite the presence of the water by-product.

Thus, there is provided an efficient method of preparing nitrone derivatives. The following examples are provided to further illustrate, and not limit, the method described herein.

EXAMPLE 1

Preparation of N-Benzylidene-t-Butylamine

To a nitrogen charged 1 liter, 3-necked round bottom flask equipped with a mechanical paddle stirrer, pot thermometer, nitrogen gas flow, and condenser was added 174 gm (167 ml; 1.64 moles) of benzaldehyde followed by 126 gm (181 ml; 1.72 moles) of t-butylamine with vigorous stirring. The temperature of the reaction mixture slowly increased from 22° C. to about 39° C. After about 1 hour, the clear, pale yellow solution became cloudy as the water formed during the reaction separated and the temperature slowly decreased. After a total of 4 hours, the two-phased reaction mixture was poured into a separatory funnel from which the lower aqueous phase (about 29 gm) was separated and removed while the yellow upper organic phase was evacuated under vacuum (aspirator; about 24" Hg) to produce a crude product of 259.2 gm (98.2% yield). Gas chromatographic analysis of the crude product (GC analysis using a 30 meter DB-1 column with a programmed temperature range increasing from 100° C. to 250° C. at 15° C. per minute increments) indicated it to be very pure N-benzylidene-t-butylamine product as reflected by a single spectral peak having a retention time of 3.72 minutes.

EXAMPLE 2

Preparation of 2-t-Butyl-3-Phenyloxaziridine 13.2 gm (0.082 moles) of the N-benzylidene-t-butylamine prepared as in Example 1 was added to a 600 ml beaker containing 28.8 gm of sodium bicarbonate (0.3428 moles) in a solution consisting of 50 ml water and 50 ml acetone. The mixture was stirred vigorously with a mechanical paddle stirrer. While stirring, 60 gm (0.098 moles) of Oxone® was added portion wise over a 3 to 5 minute period. The resulting three-phase mixture was initially bluish in color and eventually faded to a pale yellow color as the reaction proceeded. The reaction was stirred at ambient temperature for one hour and followed by GC analysis as described in Example 1. The GC analysis revealed only a trace of the starting material (very tiny peak at 3.72 minutes) and predominant conversion to the oxaziridine, a peak having a retention time of 4.45 minutes. The mixture was diluted with 300 ml of water to dissolve any salts therein. The 2-phase mixture was extracted with 100 ml of hexane. The hexane layer was separated and concentrated under vacuum to remove all solvent. The resulting, almost clear liquid, 2-t-butyl-3-phenyl oxaziridine product weighed 13.74 gm (94.7% crude yield).

EXAMPLE 3

Preparation of N-t-butylphenylnitrone

To a nitrogen charged 250 ml, 3-necked, round bottom flask equipped with a magnetic stir bar, nitrogen gas flow, pot thermometer, and condenser was added 119.3 gm (0.674 moles) of the 2-t-butyl-3-phenyloxaziridine as prepared in Example 2 and several silicon carbide boiling chips. The system was continuously flushed with nitrogen while gradually heated to 120° C. Upon reaching 120°, the heat was removed as the exothermic rearrangement brought the reaction temperature to about 134° C. before slowly subsiding. The pale yellow 2-t-butyl-3-phenyloxaziridine gradually turned to a clear, dark brown color. The reaction was cooled after a total reaction time of about 1 hour and a GC analysis, as described in Example 1, of the crude product 25 indicated a complete conversion to the corresponding nitrone (a peak having a retention time of 6.45 minutes). Upon cooling, the liquid N-t-butylphenylnitrone crystallized to form a solid having a crude yield of 109.4 gm (91.7% of theoretical yield).

EXAMPLE 4

Preparation of N-t-butylphenylnitrone Without Isolation of Reaction Intermediates To a dry 3 liter, 3-necked, round bottom flask equipped with a mechanical paddle stirrer, a nitrogen gas flow, and a condenser was added 87 gm (83.5 ml; 0.82 moles) of benzaldehyde and 63 gm (90.5 ml; 0.86 moles) of t-butylamine. The mixture was stirred for about 4 hours at room temperature to allow complete formation of N-benzylidene-t-butylamine. After removal of the nitrogen gas flow and the condenser, the reaction flask was evacuated under an aspirator (about 24" Hg vacuum) for about 15 minutes. The aspirator was detached and 288 gm (3.428 moles) of sodium bicarbonate followed by 500 ml of water and 500 ml of acetone were added to the 3-liter flask. The condenser was reattached to the flask and carefully about 600 gm (0.98 moles) of Oxone® was added portion-wise through a powder-addition funnel to the stirring reaction over a period of about 10 minutes. The reaction began to slowly foam from the evolution of carbon dioxide and turn to a bluish tinge as the temperature rose to about 35° C. The reaction was stirred for one hour after the Oxone® addition, and a GC analysis revealed a trace amount of starting imine (3.72 minutes) and a large peak representing 2-t-butyl-3-phenyl oxaziridine (4.45 minutes). The reaction was poured into a beaker containing a 2-phase solution of 3000 ml water and 300 ml toluene. Insoluble salts were filtered out and the aqueous layer separated in a separatory funnel. The upper toluene layer was placed in a 1-liter single-neck, round bottom flask and concentrated over a 30-minute period on a rotary evaporator at 50° C. under vacuum (about 24" Hg) to remove traces of acetone and water. Several silicon carbide boiling chips were added to the concentrated oxaziridine and the oxaziridine/toluene solution was refluxed at 115° C. –125° C. for 2–3 hours to form the desired N-t-butylphenylnitrone product. The excess toluene was removed under vacuum and the resulting clear brown liquid N-t-butylphenylnitrone was poured into a crystallizing dish and placed in a fume hood. Crystallization was almost immediate, affording 113.1 gm of crude crystalline N-t-butylphenylnitrone (78% theoretical yield).

By virtue of the foregoing, there is provided an efficient method for the preparation of nitrone derivatives, and in particular the preparation of PBN, without the drawbacks of traditional methods. The present method, as described in the detailed description and in the examples above, provide for crystalline-pure PBN to be prepared in high yields from readily available benzylaldehyde and t-butylamine without isolation and purification of intermediates (i.e., the N-benzylidene-t-butylamine and the 2-t-butyl-3phenyloxaziridine), and without purification of the nitrone product. Further, removal of water from the mixture during formation of the imine is unnecessary, and the imine is essentially formed to completion in less than four hours under ambient conditions. In addition, oxidation of the imine to the corresponding oxaziridine takes place readily in an aqueous acetone solution with a commercial grade of an oxidizing agent, such as Oxone®. Further, the present method is beneficial in that nitrone derivatives are prepared without use of metal catalysts, large amounts of chlorinated and toxic solvents, and expensive or commercially unavailable starting materials. While efficient in cost, the present method is also efficient from the perspective of time required for preparing the nitrone derivatives, and amenability to scaling the reaction to commercial volumes.

While the present invention has been illustrated by the description of embodiments thereof, and while the embodiments have been described in considerable detail, the description is not intended to restrict or in any way limit the scope of the appended claims to such detail. Additional advantages and modifications will be readily apparent to those of ordinary skill in the art. The invention in its broader aspects is therefore not limited to the specific details, representative structures, method, and examples shown and described. For example, while the structures of formulae (VII) and (X) are illustrated as the trans configuration around the exocyclic double bond, the present invention is not so limited and these formulae are intended to generally include nitrones having a cis configuration as well. Accordingly, departures may be made from such details without departing from the scope or spirit of the general inventive concept.

What is claimed is:

1. A method of preparing a nitrone compound having a general formula (I):

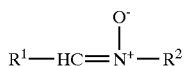

wherein $R_1$ and $R_2$, independently, are selected from the group consisting of a substituted or unsubstituted straight, branched, or cyclic alkyl, alkenyl, alkynyl, aryl, heteroaryl, alkaryl, alkoxyl, halo-alkyl, and combinations thereof, alternatively, $R_1$ and $R_2$ taken together with the carbon and nitrogen to which they are attached form a 5–8 membered ring containing 0–1 additional heteroatoms selected from the group consisting of N, O, and S, the method comprising the steps of:

reacting an imine compound having a general formula (II)

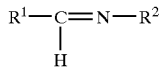

wherein $R_1$ and $R_2$ are as defined above, with an oxidizing agent having a general formula (III)

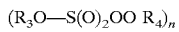

wherein $R_3$ and $R4$, independently, are selected from the group consisting of $NH_4$, Na, K, Li, and substituted or unsubstituted straight, branched or cyclic $C_1$–$C_{10}$ alkyl, and n is 1, in a solution to form an oxaziridine compound having a general formula (IV)

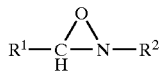

wherein $R_1$ and $R_2$ are as defined above and the imine compound is in a concentration of at least about 0.1M in the solution; and rearranging the oxaziridine compound of formula (IV) to form a nitrone compound of formula (I).

2. The method of claim 1 wherein $R_3$ and $R_4$ independently are selected from the group consisting of $NH_4$, Na, K, Li, and $C_1$–$C_5$ substituted or unsubstituted straight, branched or cyclic alkyl, and n is an integer selected from 1, 2, and 3.

3. The method of claim 1 wherein the oxidizing agent is a potassium monoperoxysulfate compound.

4. The method of claim 1 wherein the imine compound is in a concentration range of from about 0.1M to about 1.0M in the solution.

5. The method of claim 1 wherein the imine compound is in a concentration range of from about 0.5M to about 1.0M in the solution.

6. The method of claim 1 further comprising the step of: reacting an aldehyde having a general formula (V)

with an amine compound having a general formula (VI)

to form the imine compound of formula (II), wherein $R_1$ and $R_2$, independently, are selected from the group consisting of a substituted or unsubstituted straight, branched, or cyclic alkyl, alkenyl, alkynyl, aryl, heteroaryl, alkaryl, alkoxyl, halo-alkyl, and combinations thereof, and alternatively, $R_1$ and $R_2$ are attached by a linker containing 1–4 carbon atoms including 0–1 heteroatoms selected from the group consisting of N, O, and S.

7. The method of claim 1 wherein the oxaziridine compound of formula (IV) is rearranged in the absence of a diluent.

8. The method of claim 1 wherein the step of rearranging the oxaziridine compound of formula (IV) comprises heating the oxaziridine compound to form the nitrone compound of formula (I).

9. The method of claim 1 wherein the oxaziridine compound of formula (IV) is heated to a temperature in the range of from about 110° C. to about 150° C. to rearrange the oxaziridine compound to form the nitrone compound.

10. The method of claim 1 wherein the oxaziridine compound of formula (IV) is heated for a time period in the range of from about 1 hour to about 10 hours.

11. The method of claim 1 wherein the nitrone compound prepared is phenyl-tert-butyl nitrone.

12. The method of claim 1 wherein the imine compound of formula (II) is formed in a reactor without removal of water of reaction from the reactor.

13. A method of preparing a nitrone compound having a general formula (VII)

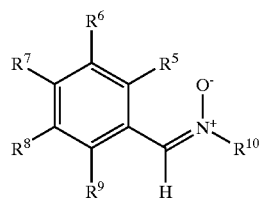

wherein $R^5$, $R^6$, $R^7$, $R^8$ and $R^9$ are independently selected from the group consisting of H, substituted or unsubstituted straight, branched, or cyclic alkyl, alkenyl, alkynyl, aryl, heteroaryl, alkaryl, alkoxyl, halo, cyano, nitro, and combinations thereof, alternatively any two adjacent $R^5$, $R^6$, $R^7$, $R^8$ and $R^9$ groups taken together with the carbons to which they are attached form a 5–8 membered ring including 0–2 heteroatoms selected from the group consisting of O, N, and S, $R^{10}$ is a substituted or unsubstituted straight, branched, or cyclic alkyl, the method comprising the steps of:

(a) reacting an aldehyde compound having a general formula (VIII)

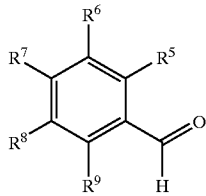

wherein $R^5$, $R^6$, $R^7$, $R^8$ and $R^9$ are as defined in general formula (VII), with an amine compound having a general formula (IX)

wherein $R^{10}$ is as defined in general formula (VII), to form an imine compound having a general formula (X)

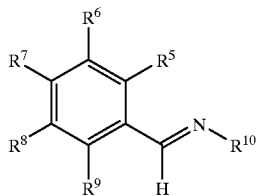

wherein $R^5$, $R^6$, $R^7$, $R^8$, $R^9$ and $R^{10}$ are as defined in general formula (VII);

(b) reacting the imine compound of formula (X) with an oxidizing agent having a general formula (XI)

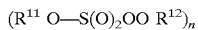

wherein $R^{11}$ and $R^{12}$, independently, are selected from the group consisting of $NH_4$, Na, K, Li, and straight, branched or cyclic $C_1$–$C_{10}$ alkyl, and n is 1, in a solution having at least about 0.1M concentration of the imine compound in the solution, to form an oxaziridine compound having a general formula (XII)

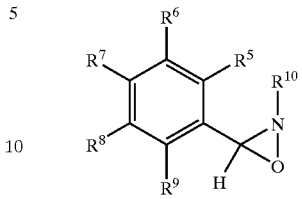

wherein $R^5$, $R^6$, $R^7$, $R^8$, $R^9$ and $R^{10}$ are as defined in general for a (VII); and (c) rearranging the oxaziridine compound of formula (XII) form the nitrone compound of formula (VII).

14. The method of claim 13 wherein the oxaziridine compound is rearranged in the absence of a diluent.

15. The method of claim 13 wherein the oxaziridine compound is heated to thermally rearrange the oxaziridine compound to form the nitrone compound.

16. The method of claim 13 wherein the oxaziridine compound is heated to a temperature in the range of from about 110° C. to about 150° C. to form the nitrone compound.

17. The method of claim 13 wherein the oxidizing agent is a potassium monoperoxysulfate compound.

18. The method of claim 13 wherein the imine compound is in a concentration range of from about 0.1M to about 1.0M in the solution.

19. The method of claim 13 wherein the imine compound is in a concentration range of from about 0.5M to about 1.0M in the solution.

20. The method of claim 13 wherein the nitrone compound prepared is phenyl-tert-butyl nitrone.

* * * * *

UNITED STATES PATENT AND TRADEMARK OFFICE
CERTIFICATE OF CORRECTION

PATENT NO.    : 6,762,322 B1
DATED         : July 13, 2004
INVENTOR(S)   : Dane Kenton Parker It is certified that error appears in the above-identified patent and that said Letters Patent is hereby corrected as shown below:

Title page,
Item [73], Assignee, "Goodyear Tire & Rubber Company" should read -- The Goodyear Tire & Rubber Company --.
Item [56], References Cited, OTHER PUBLICATIONS,
"Risnik et al," reference, "Kauchuk i Rezina, No. 6," should read -- Kauchuk i Rezina, No. 6, --.
"Grishin et al," reference, "Ser. A Vol. 43, No. 10," should read -- Ser. A, Vol. 43, No. 10, --.
"Christensen et al," reference, "by the Permangante Ion," should read -- by the Permanganate Ion, --.
Item [57], ABSTRACT, "with a peroxysulfacte oxidizing agent" should read -- with a peroxysulfate oxidizing agent --.

Column 2,
Line 15, "reduction of 2-methyl 2-nitropropane," should read -- reduction of 2-methyl-2-nitropropane, --.

Column 3,
Line 10, "wherein R1 and R2, are independently selected" should read -- wherein R1 and R2 are independently --.

Column 8,
Line 13, "encompass all compounds formed" should read -- encompasses all compounds --.
Line 48, "can be optionally be substituted with" should read -- can be optionally substituted with --.

Column 9,
Line 19, "cyclohexynitrone" should read -- cyclohexylnitrone --.
Line 19, "N-t-penyl-" should read -- N-t-pentyl --.
Line 39, "4,4diethyl-1-" should read -- 4,4-diethy-1- --.
Line 44, "may be joined together form" should read -- may be joined together to form --.

UNITED STATES PATENT AND TRADEMARK OFFICE
CERTIFICATE OF CORRECTION

PATENT NO. : 6,762,322 B1
DATED : July 13, 2004
INVENTOR(S) : Dane Kenton Parker It is certified that error appears in the above-identified patent and that said Letters Patent is hereby corrected as shown below:

Column 13,
Line 6, "during the reaction separated" should read -- during the reaction, separated --.
Line 55, "of the crude product 25 indicated" should read -- of the crude product indicated --.

Column 14,
Line 41, "provide for" should read -- provides for --.
Line 46, "2-t-butyl-3phenyloxaziridine" should read -- 2-t-butyl-3-phenyloxaziridine --.

Column 18,
Line 15, "are as defined in general for a (VII);" should read -- are as defined in general formula (VIII) --.

Signed and Sealed this

Twenty-second Day of February, 2005

JON W. DUDAS
*Director of the United States Patent and Trademark Office*